(12) United States Patent
Tamura

(10) Patent No.: US 6,365,142 B1
(45) Date of Patent: *Apr. 2, 2002

(54) HAIR CONDITIONING COMPOSITIONS WHICH PROVIDE SUPERIOR WET HAIR FEEL ATTRIBUTES AND WHICH ARE SUBSTANTIALLY FREE OF QUATERNARY AMMONIUM COMPOUNDS

(75) Inventor: Haruo Tamura, Kobe (JP)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/068,633

(22) PCT Filed: Nov. 8, 1996

(86) PCT No.: PCT/US96/18011

§ 371 Date: May 5, 1998

§ 102(e) Date: May 5, 1998

(87) PCT Pub. No.: WO97/31617

PCT Pub. Date: Sep. 4, 1997

(30) Foreign Application Priority Data

Feb. 28, 1996 (AU) ............................................. 45808/96

(51) Int. Cl.⁷ .............................. A61K 7/06; A61K 7/11
(52) U.S. Cl. ................. 424/70.17; 424/70.1; 424/70.11
(58) Field of Search .............................. 424/70.1, 70.28, 424/401, 70.12, 70.17, 70.19, 70.11; 514/880

(56) References Cited

U.S. PATENT DOCUMENTS 4,726,945 A    2/1988   Patel et al.
4,911,919 A    3/1990   Patel et al. .................... 424/70
4,976,956 A    12/1990  Noe
5,328,685 A    7/1994   Janchitraponvej et al.
5,384,114 A *  1/1995   Dowell et al.

FOREIGN PATENT DOCUMENTS

| EP | 0562637 A1 | 9/1993 | ............ A61K/7/06 |
| EP | 0562639 A1 | 9/1993 | ............ A61K/7/08 |
| JP | 62-51612 A | 3/1987 | ............ A61K/7/06 |
| JP | 5-271035 A | 10/1993 | ............ A61K/7/06 |

* cited by examiner

Primary Examiner—Thurman K. Page
Assistant Examiner—Brian K. Seidleck
(74) Attorney, Agent, or Firm—Linda M. Sivik; Brahm J. Gorstanje; Tara M. Rosnell

(57) ABSTRACT

Mild hair conditioning compositions comprise by weight: (a) from about 0.5% to about 5.0% of an amidoamine or mixture of amidoamines having the following general formula:

$$R^1CONH(CH_2)_mN(R^2)_2$$

wherein $R^1$ is a residue of $C_{11}$ to $C_{24}$ fatty acids, $R^2$ is a $C_1$ to $C_4$ alkyl, and m is an integer from 1 to 4; (b) from about 0.05% to about 2.0% of an acid or mixture of acids; (c) from about 0.1% to about 15% of a fatty compound selected from the group consisting of fatty alcohols, fatty acids, fatty alcohol derivatives, fatty acid derivatives, and mixtures thereof; (d) water; and (e) optionally from about 0.05% to 5.0% of a detersive surfactant; wherein the compositions have a pH of from about 4.5 to about 6 or a mole ratio of from about 1:0.3 to about 1:1.0 of components (a) to (b), and wherein the compositions are substantially free of quaternary ammonium compounds.

12 Claims, No Drawings

HAIR CONDITIONING COMPOSITIONS WHICH PROVIDE SUPERIOR WET HAIR FEEL ATTRIBUTES AND WHICH ARE SUBSTANTIALLY FREE OF QUATERNARY AMMONIUM COMPOUNDS

This application is a 371 of PCT/US96/18011, filed Nov. 8, 1996.

TECHNICAL FIELD

The present invention relates to mild hair conditioning compositions.

BACKGROUND

Scalp hair becomes soiled due to its contact with the surrounding environment and from sebum secreted from the hair follicles. The build-up of sebum and environmental soiling can cause the hair to have a dirty or greasy feet, and an unattractive appearance. In order to ameliorate these effects, it is necessary to shampoo the hair with regularity.

Shampooing the hair removes excess sebum and other environmental soiling but has disadvantages in that the hair can be left in a wet, tangled, and relatively unmanageable state. Shampooing can also result in the hair becoming dry due to the removal of natural oils or other hair moisturizing materials. After shampooing, the hair can also suffer from a perceived loss of "softness." Frequent shampooing also contributes to the phenomena of "split ends," particularly for long hair. Split ends refers to a condition wherein the ends of the hair are split into two or more shafts, resulting in a frizzy appearance.

A variety of approaches have been developed to condition the hair. These range from post-shampooing hair rinses, to leave-on hair conditioners, to the inclusion of hair conditioning components in shampoos. Although many consumers prefer the ease and convenience of a shampoo which includes conditioners, a substantial proportion of consumers prefer the more conventional conditioner formulations which are applied to the hair as a separate step from shampooing, usually subsequent to shampooing. These hair conditioners typically are formulated as a thickened product, such as a gel or cream, for ease of dispensing and application to the hair.

Consumers prefer conditioners which provide dry combing benefits and wet hair feel attributes such as ease of spreading and hair softness during rinsing. In addition consumers desire new conditioners which is mild for scalp, hair and skin.

Hair rinse conditioners have conventionally been based on the combination of a cationic surfactant, which are generally a quaternary ammonium compound such as ditallow dimethyl ammonium chloride, and fatty alcohols, such as cetyl and stearyl alcohols. This combination results in a gel-network structure which provides the compositions with a thick, creamy rheology. However, quaternary ammonium compounds are not sufficient to provide hair softness and ease of spreading during rinsing and dry combing. In addition, quaternary ammonium compounds may cause harshness and irritation to scalp, hair and/or skin. Further, some of the quaternary ammonium compounds such as ditallowdimethylammonium chloride are not biodegradable, and consequently are not preferred in view of enviromental requirements.

Therefore, there is a desire of providing hair conditioning compositions which are substantially free of quaternary ammonium compounds.

In order to improve the above problem, Japanese Patent Publication (laid-open) No. 62-51612 discloses a hair treatment composition comprising amidoamine derivatives and carboxylic acid derivatives which provides conditioning efficacy for drying. Japanese Patent Publication (laid-open) No. 64-6210 discloses a hair conditioning composition comprising bis(2-alkyl-N-hydroxy ethyl imidazoline) chloracetic acid complex amphoteric surfactant and amidoamine which provides hair softness and smoothness. Japanese Patent Publication (laid-open) No. 5-271036 discloses a hair treating composition comprising amidoamine compounds, amphoteric surfactants, higher fatty alcohol, organic acid and water.

Therefore, there is a desire of providing a hair conditioning composition which is very mild for scalp, hair and/or skin, and which provides both dry combing benefits and wet hair feel attributes during rinsing.

It has now been found that hair conditioning compositions substantially free of quaternary ammonium compounds can be provided in the form of a product which is very mild for scalp, hair and/or skin, and which have excellent wet hair feel, spreadability, and rinseability, as well as providing glossiness, and dry combing benefits while being formulated in a rinse on or rinse off conditioner, through the use of amidoamines, acids, and fatty compounds.

SUMMARY

The present invention relates to hair conditioning compositions comprising by weight:
(a) from about 0.5% to about 5.0% of an amidoamine or mixture of amidoamines;
(b) from about 0.05% to about 2.0% of an acid or mixtures of acids;
(c) from about 0.1% to about 15% of a fatty compound selected from the group consisting of fatty alcohols, fatty acids, fatty alcohol derivatives, fatty acid derivatives, and mixtures thereof; and
(d) water;
wherein the pH of the composition is from about 4.5 to about 6, or the mole ratio of the amidoamine to the acid is from about 1:0.3 to about 1:1.0.

Such compositions satisfy the need for a hair conditioning composition substantially free of quaternary ammonium compounds having excellent wet hair feel, spreadability, and rinseability, as well as providing glossiness, and dry combing benefits while being formulated in a leave on or rinse off conditioner having a thick, cream-type rheology with excellent spreading, and slick feel during speading and rinsing.

These and other objects and benefits as may be discussed or apparent may be obtained with the present invention, which is discussed below.

DETAILED DESCRIPTION

All percentages herein are by weight of the compositions unless otherwise indicated. All ratios are weight ratios unless otherwise indicated. All percentages, ratios, and levels of ingredients referred to herein are based on the actual amount of the ingredient, and do not include solvents, fillers, or other materials with which the ingredient may be combined as commercially available products, unless otherwise indicated.

The invention hereof can compromise, consist of, or consist essentially of the essential elements described herein as well as any of the preferred or optional ingredients also described herein.

AMIDOAMINES

The compositions of the present invention comprise by weight from about 0.5% to about 5.0%, preferably from about 1.0% to about 3.0%, more preferably from about 1.5% to about 2.5%, of an amidoamine or mixture of amidoamines.

The amidoamines hereof have the following general formula:

$$R^1CONH(CH2)_mN(R^2)_2$$

wherein $R^1$ is a residue of $C_{11}$ to $C_{24}$ fatty acids, $R^2$ is a $C_1$ to $C_4$ alkyl, and m is an integer from 1 to 4.

Preferred amidoamines useful in the present invention include stearamidopropyldimethylamine, stearamidopropyldiethylamine, stearamidoethyldiethylamine, stearamidoethyldimethylamine, palmitamidopropyldimethilamine, palmitamidopropyldiethilamine, palmitamidoethyldiethilamine, palmitamidoethyldimethilamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, and mixtures thereof; more preferably stearamidopropyldimethylamine, stearamidoethyldiethylamine, and mixtures thereof.

ACIDS

The compositions of the present invention comprise by weight from about 0.05% to about 2.0%, preferably from about 0.2% to about 1.5%, and more preferably from about 0.3% to about 1.0% of an acid or mixture of acids.

The acids in this invention can be any acid used by those skilled in the art, including organic acids and inorganic acids. Preferred acids useful in the present invention include L-glutamic acid, lactic acid, hydrochloric acid, malic acid, succinic acid, acetic acid, fumaric acid, 1-glutamic acid hydrochloride, tartaric acid, and mixtures thereof; more preferably L-glutamic acid, lactic acid, hydrochloric acid, and mixtures thereof. Citric acid is preferably not used.

Preferably, the mole ratio of amidoamines of the present invention to acids of the present invention is from about 1:0.3 to about 1:1, more preferably from about 1:0.5 to about 1:0.9.

FATTY COMPOUNDS

The compositions of the present invention comprise by weight from about 0.1 to about 15%, preferably from about 1% to about 10% of a fatty compound selected from the group consisting of fatty alcohols, fatty acids, fatty alcohol derivatives, fatty acid derivatives, and mixtures thereof. It is recognized that the compounds disclosed in this section of the specification can in some instances fall into more than one classification, e.g., some fatty alcohol derivatives can also be classified as fatty acid derivatives. Also, it is recognized that some of these compounds can have properties as nonionic surfactants and can alternatively be classified as such. However, a given classification is not intendend to be a limitation on that particular compound, but is done so for convenience of classification and nomenclature. Nonlimiting examples of the fatty alcohols, fatty acids, fatty alcohol derivatives, and fatty acid derivatives are found in International Cosmetic Ingredient Dictionary, Fifth Edition, 1993, and CTFA Cosmetic Ingredient Handbook, Second Edition, 1992, both of which are incorporated by reference herein in their entirety.

The fatty alcohols useful herein are those having from about 10 to about 30 carbon atoms, preferably from about 12 to about 22 carbon atoms, and more preferably from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and mixtures thereof. Especially preferred fatty alcohols are those selected from the group consisting of cetyl alcohol, stearyl alcohol, isostearyl alcohol, oleyl alcohol, and mixtures thereof.

The fatty acids useful herein are those having from about 10 to about 30 carbon atoms, preferably from about 12 to about 22 carbon atoms, and more prefeably from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, and mixtures thereof. Especially preferred for use herein are the fatty acids selected from the group consisting of palmitic acid, stearic acid, and mixtures thereof.

The fatty alcohol derivatives are defined herein to include alkyl ethers of fatty alcohols, alkoxylated fatty alcohols, alkyl ethers of alkoxylated fatty alcohols, esters of fatty alcohols and mixtures thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth45, which are ethylene glycol ethers of cetyl alcochol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1–C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and mixtures of all of the foregoing compounds. Preferred for use herein are steareth-2, steareth-4, ceteth-2, and mixtures thereof.

The fatty acid derivatives are defined herein to include fatty acid esters of the fatty alcohols as defined above in this section, fatty acid esters of the fatty alcohol derivatives as defined above in this section when such fatty alcohol derivatives have an esterifiable hydroxyl group, fatty acid esters of alcohols other than the fatty alcohols and the fatty alcohol derivatives described above in this section, hydroxy-substitued fatty acids, and mixtures thereof. Nonlimiting examples of fatty acid derivatives inlcude ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and mixtures thereof. Preferred for use herein are glycerol monostearate, 12-hydroxy stearic acid, and mixtures thereof.

Highly preferred fatty compounds are cetyl alcohol, stearyl alcohol, and mixtures thereof.

WATER

The compositions of the present invention comprise water. The water phase can optionally include other liquid, water-miscible or water-soluble solvents such as lower alkyl alcohols, e.g. $C_1$–$C_5$ alkyl monohydric alcohols, preferably $C_2$–$C_3$ alkyl alcohols. However, the fatty compound must be miscible in the aqueous phase of the composition. Said fatty compound can be naturally miscible in the aqueous phase or can be made miscible through the use of cosolvents or surfactants.

The compositions of the present invention have a pH of from about 4.5 to about 6.

QUATERNARY AMMONIUM COMPOUNDS

The compositions of the present invention are substantially free of quaternary ammonium compounds which are commonly used in the art. Examples of quaternary ammonium compounds are those of the general formula:

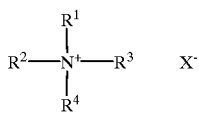

wherein $R^1$–$R^4$ are independently an aliphatic group of from about 1 to about 22 carbon atoms or an aromatic, alkoxy, polyoxyalkylene, alkylamido, hydroxyalkyl, aryl or alkylaryl group having from about 1 to about 22 carbon atoms; and X is a salt-forming anion such as those selected from halogen, (e.g. chloride, bromide), acetate, citrate, lactate, glycolate, phosphate, nitrate, sulfate, and alkylsulfate radicals. The aliphatic groups may contain, in addition to carbon and hydrogen atoms, ether linkages, and other groups such as amino groups.

OTHER CONDITIONING AGENTS

The compositions of the present invention may comprise by weight from about 0.1% to about 20.0%, preferably from about 1.0% to about 15.0%, and more preferably from about 2.0% to about 10% of other conditioning agents known in the industry. Suitable conditioning agents are cationic polymers, volatile silicones (including soluble and insoluble silicones), nonvolatile silicones (including soluble and insoluble silicones), nonvolatile hydrocarbons, nonvolatile hydrocarbon esters, and proteins.

Cationic Polymer Conditioning Agent

The compositions of the present invention can comprise one or more cationic polymer conditioning agents. The cationic polymer conditioning agents will preferably be water soluble.

By "water soluble" cationic polymer, what is meant is a polymer which is sufficiently soluble in water to form a substantially clear solution to the naked eye at a concentration of 0.1% in water (distilled or equivalent) at 25° C. Preferably, the polymer will be sufficiently soluble to form a substantially clear solution at 0.5% concentration, more preferably at 1.0% concentration.

As used herein, the term "polymer" shall include materials whether made by polymerization of one type of monomer or made by two (i.e., copolymers) or more types of monomers.

The cationic polymers hereof will generally have a weight average molecular weight which is at least about 5,000, typically at least about 10,000, and is less than about 10 million. Preferably, the molecular weight is from about 100,000 to about 2 million. The cationic polymers will generally have cationic nitrogen-containing moieties such as quaternary ammonium or cationic amino moieties, and mixtures thereof.

The cationic charge density is preferably at least about 0.1 meq/gram, more preferably at least about 1.5 meq/gram, even more preferably at least abut 1.1 meq/gram, still more preferably at least about 1.2 meq/gram. Cationic charge density of the cationic polymer can be determined according to the Kjeldahl Method. Those skilled in the art will recognize that the charge density of amino-containing polymers may vary depending upon pH and the isoelectric point of the amino groups. The charge density should be within the above limits at the pH of intended use.

Any anionic counterions can be utilized for the cationic polymers so long as the water solubility criteria is met. Suitable counterions include halides (e.g., Cl, Br, I, or F, preferably Cl, Br, or I), sulfate, and methylsulfate. Others can also be used, as this list is not exclusive.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982).

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the composition. In general, secondary and tertiary amines, especially tertiary amines, are preferred.

Amine-substituted vinyl monomers can be polymerized in the amine form, and then optionally can be converted to ammonium by a quaternization reaction. Amines can also be similarly quaternized subsequent to formation of the polymer. For example, tertiary amine functionalities can be quaternized by reaction with a salt of the formula R'X wherein R' is a short chain alkyl, preferably a $C_1$–$C_7$ alkyl, more preferably a $C_1$–$C_3$ alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic polymers hereof can comprise mixtures of monomer units derived from amine- and/or quaternary ammonium-subsituted monomer and/or compatible spacer monomers.

Suitable cationic hair conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from Gaf Corporation (Wayne, N.J., USA) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homo- and co-polymers of unsaturated carboxylic acids having from 3 to 5 carbon atoms, as described in U.S. Pat. No. 4,009,256, incorporated herein by reference.

Other cationic polymers that can be used include polysaccharide polymers, such as cationic cellulose derivatives and cationic starch derivatives.

Cationic polysaccharide polymer materials suitable for use herein include those of the formula:

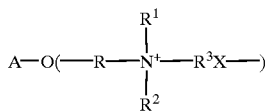

wherein: A is an anhydroglucose residual group, such as a starch or cellulose anhydroglucose residual, R is an alkylene oxyalkylene, polyoxyalkylene, or hydroxyalkylene group, or combination thereof, $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion, as previously described.

Cationic cellulose is available from Amerchol Corp. (Edison, N.J., USA) in their Polymer JR® and LR® series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted opoxide, referred to in the industry (CTFA) as Polyquaternium 24. These materials are available from Amerchol Corp. (Edison, N.J., USA) under the tradename Polymer LM-200®.

Other cationic polymers that can be used include cationic guar gum derivatives, such as guar hydroxypropyltrimonium chloride (commercially available from Celanese Corp. in their Jaguar R series). Other materials include quaternary nitrogen-containing cellulose ethers (e.g., as described in U.S. Pat. No. 3,962,418, incorporated herein by reference), and copolymers of etherified cellulose and starch (e.g., as described in U.S. Pat. No. 3,958,581, incorporated herein by reference.)

As discussed above, the cationic polymer hereof is water soluble. This does not mean, however, that it must be soluble in the composition. Preferably however, the cationic polymer is either soluble in the composition, or in a complex coacervate phase in the composition formed by the cationic polymer and anionic material. Complex coacervates of the cationic polymer can be formed with anionic surfactants or with anionic polymers that can optionally be added to the compositions hereof (e.g., sodium polystyrene sulfonate).

Silicone Conditioning Agent

The compositions hereof can include volatile soluble or insoluble, or nonvolatile soluble or insoluble silicone conditioning agents. By soluble what is meant is that the silicone conditioning agent is miscible with the aqueous carrier of the composition so as to form part of the same phase. By insoluble what is meant is that the silicone forms a separate, discontinuous phase from the aqueous carrier, such as in the form of an emulsion or a suspension of droplets of the silicone.

The silicone hair conditioning agent can be used in the compositions hereof at levels of from about 0.05% to about 20% by weight of the composition, preferably from about 0.1% to about 6%, more preferably from about 0.5% to about 5%, still more preferably from about 0.5% to about 3%.

Soluble silicones include silicone copolyols, such as dimethicone copolyols, e.g. polyether siloxane-modified polymers, such as polypropylene oxide, polyethylene oxide modified polydimethylsiloxane, wherein the level of ethylene and/or propylene oxide is sufficient to allow solubility in the composition.

Preferred, however, are insoluble silicones. The insoluble silicone hair conditioning agent for use herein will preferably have viscosity of from about 1,000 to about 2,000,000 centistokes at 25° C., more preferably from about 10,000 to about 1,800,000, even more preferably from about 100,000 to about 1,500,000. The viscosity can be measured by means of a glass capillary viscometer as set forth in Dow Corning Corporate Test Method CTM0004, Jul. 20, 1970.

Suitable insoluble, nonvolatile silicone fluids include polyalkyl siloxanes, polyaryl siloxanes, polyalkylaryl siloxanes, polyether siloxane copolymers, and mixtures thereof. Other insoluble, nonvolatile silicone fluids having hair conditioning properties can also be used. The term "nonvolatile" as used herein shall mean that the silicone has a boiling point of at least about 260° C., preferably at least about 275° C., more preferably at least about 300° C. Such materials exhibit very low or no significant vapor pressure at ambient conditions. The term "silicone fluid" shall mean flowable silicone materials having a viscosity of less than 1,000,000 centistokes at 25° C. Generally, the viscosity of the fluid will be between about 5 and 1,000,000 centistokes at 25° C., preferably between about 10 and about 300,000 centistokes.

Silicone fluids hereof also include polyalkyl or polyaryl siloxanes with the following structure;

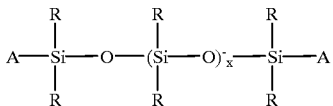

wherein R is alkyl or aryl, and x is an integer from about 7 to about 8,000. "A" represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

The nonvolatile polyalkylsiloxane fluids that may be used include, for example, polydimethylsiloxanes. These siloxanes are available, for example, from the General Electric Company in their ViscasilR and SF 96 series, and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

Especially preferred, for enhancing the shine characteristics of hair, are highly arylated silicones, such as highly phenylated polyethyl silicone having refractive indices of about 1.46 or higher, especially about 1.52 or higher. When these high refractive index silicones are used, they should be mixed with a spreading agent, such as a surfactant or a silicone resin, as described below to decrease the surface tension and enhance the film forming ability of the material.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide level should be sufficiently low to prevent solubility in the composition hereof.

References disclosing suitable silicone fluids include U.S. Pat. No. 2,826,551, Geen; U.S. Pat. No. 3,964,500, Drakoff, issued Jun. 22, 1976; U.S. Pat. No. 4,364,837, Pader; and British Patent 849,433, Woolston. All of these patents are incorporated herein by reference. Also incorporated herein by reference is Silicon Compounds distributed by Petrarch Systems, Inc., 1984. This reference provides an extensive (though not exclusive) listing of suitable silicone fluids.

Another silicone hair conditioning material that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979 and Noll, Walter, Chemistry and Technology of Silicones, New York: Academic Press 1968. Also describing silicone gums are General Electric Silicone Rubber Product Data Sheets SE 30, SE 33, SE 54 and SE 76. All of these described references are incorporated herein by reference. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane) (methylvinylsiloxane) copolymer and mixtures thereof.

Preferably the silicone hair conditioning agent comprises a mixture of a polydimethylsiloxane gum, having a viscosity greater than about 1,000,000 centistokes and polydimethylsiloxane fluid having a viscosity of from about 10 centistokes to about 100,000 centistokes, wherein the ratio of gum to fluid is from about 30:70 to about 70:30, preferably from about 40:60 to about 60:40.

An optional ingredient that can be included in the silicone conditioning agent is silicone resin. Silicone resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Silicone resins can enhance deposition of silicone on the hair and can enhance the glossiness of hair with high refractive index volumes.

Background material on silicones including sections discussing silicone fluids, gums, and resins, as well as manufacture of silicones, can be found in Encyclopedia of Polymer Science and Engineering, Volume 15, Second Edition, pp 204–308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH3)3SiO).5$; D denotes the difunctional unit $(CH3)2SiO$; T denotes the trifunctional unit (CH3)SiO1.5; and Q denotes the quadri- or tetra-functional unit SiO2. Primes of the unit symbols, e.g., M', D', T, and Q' denote substituents other than methyl, and must be specifically defined for each occurrence. Typical alternate substituents include groups such as vinyl, phenyls, amines, hydroxyls, etc. The molar ratios of the various units either in terms of subscripts to the symbols indicating the total number of each type of unit in the silicone (or an average thereof or as specifically indicated ratios in combination with molecular weight complete the description of the silicone material under the MDTQ system. Higher relative molar amounts of T, Q, T' and/or Q' to D, D', M and/or or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MQ and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

OTHER INGREDIENTS

The compositions herein can contain a variety of other optional components suitable for rendering such compositions more cosmetically or aesthetically acceptable or to provide them with additional usage benefits. Such conventional optional ingredients are well-known to those skilled in the art.

A wide variety of additional ingredients can be formulated into the present composition. These include: other conditioning agents such as mineral oil, propylene glycol, coconut oil, palm oil, hydrolysed collagen and hydrolysed keratin; hair-hold polymers; detersive surfactants such as anionic, nonionic, amphoteric, and zwitterionic surfactants; additional thickening agents and suspending agents such as xanthan gum, guar gum, hydroxyethyl cellulose, methyl cellulose, hydroxyethylcellulose, starch and starch derivatives; viscosity modifiers such as methanolamides of long chain fatty acids such as cocomonoethanol amide; crystalline suspending agents; pearlescent aids such as ethylene glycol distearate; preservatives such as benzyl alcohol, methyl paraben, propyl paraben and imidazolidinyl urea; polyvinyl alcohol; ethyl alcohol; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents, such as the thioglycolates; perfumes; sequestering agents, such as disodium ethylenediamine tetra-acetate; and polymer plasticizing agents, such as glycerin, disobutyl adipate, butyl stearate, and propylene glycol. Such optional ingredients generally are used individually at levels from about 0.01% to about 10.0%, preferably from about 0.05% to about 5.0% by weight of the composition.

METHOD OF USE

The hair conditioning compositions of the present invention are used in conventional ways to provide the conditioning and other benefits of the present invention. Such method of use depends upon the type of composition employed but generally involves application of an effective amount of the product to the hair, which may then be rinsed from the hair (as in the case of hair rinses) or allowed to remain on the hair (as in the case of gels, lotions, and creams). "Effective amount" means an amount sufficient enough to provide a dry combing benefit. In general, from about 1 g to about 50 g is applied to the hair on the scalp. The composition is distributed throughout the hair, typically by rubbing or massaging the hair and scalp. Preferably, the composition is applied to wet or damp hair prior to drying of the hair. After such compositions are applied to the hair, the hair is dried and styled in accordance with the preference of the user. In the alternative, the composition is applied to dry hair, and the hair is then combed or styled in accordance with the preference of the user.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name, or otherwise defined below.

*[1] An 85%/15% (wt. basis) mixture of D5 Cyclomethicone and dimethicone gum (weight average molecular weight of about 400,000 to about 600,000).

*[2] An 75%/25% (wt. basis) mixture of D5 Cyclomethicone and dimethicone gum (weight average molecular weight of about 400,000 to about 600,000).

*[3] Methylchloroisothiazoline (and) methylisothiazoline, a preservative from Rohm & Haas Co., (Philadelphia, Pa., USA).

Examples I–IV

Hair rinse compositions of the present invention are prepared as follows:

| Component (Wt. %) | Ex. I | Ex. II | Ex. III | Ex. IV |
|---|---|---|---|---|
| Stearamidopropyl-dimethylamine | 3.00 | 2.00 | 2.00 | 1.00 |
| L-Glutamic Acid | 0.96 | 0.64 | 0.64 | 0.16 |
| Cetyl Alcohol | 3.00 | 4.20 | 6.00 | 1.00 |
| Stearyl Alcohol | 2.00 | 2.80 | 4.00 | 1.00 |
| Silicone Mixture A*[1] | 5.00 | 4.20 | 3.00 | 1.00 |
| Kathon CG*[3] | 0.03 | 0.03 | 0.03 | 0.03 |
| Benzyl Alcohol | 0.50 | 0.40 | 0.50 | 0.25 |
| Methyl Paraben | — | — | 0.20 | 0.20 |
| Propyl Paraben | — | — | 0.10 | 0.10 |
| EDTA | 0.10 | 0.10 | — | 0.10 |
| Disodium EDTA | — | — | 0.13 | — |
| Perfume | 0.25 | 0.25 | 0.50 | 0.20 |
| Water | 85.16 | 85.38 | 82.90 | 94.96 |

For Examples I through IV, water, stearamidopropyidimethyl-amine and L-glutamic acid are mixed at temperature above 70° C. Then cetyl alcohol, stearyl alcohol and benzyl alcohol are added with agitation. After cooled down below 60° C., silicone mixture, Kathon CG and perfume are added with agitation, then cooled down to about 30° C.

In the above Example I, II and IV, EDTA is added prior to cooling. For Example III, disodium EDTA is added prior to or after cooling. For Examples III and IV, methyl and propyl parabens are added prior to cooling. The obtained products show dry combing benefits and wet hair feel attributes.

Examples V–VIII

Hair rinse compositions of the present invention are prepared as follows:

| Component (Wt. %) | Ex. V | Ex. VI | Ex. VII | Ex. VIII |
|---|---|---|---|---|
| Stearamidopropyl-dimethylamine | 3.00 | 2.00 | 3.00 | 3.00 |
| L-Glutamic Acid | 0.96 | — | — | 0.96 |
| Lactic Acid (90%) | — | 0.43 | 0.65 | — |
| Cetyl Alcohol | 3.00 | 4.20 | 3.00 | 3.00 |
| Stearyl Alcohol | 2.00 | 2.80 | 2.00 | 2.00 |
| Silicone Mixture A[*1] | 5.00 | 4.20 | 5.00 | — |
| Silicone Mixture B[*2] | — | — | — | 3.00 |
| Kathon CG[*3] | — | 0.03 | 0.03 | 0.03 |
| Glydant | 0.20 | — | — | — |
| Benzyl Alcohol | 0.50 | 0.40 | 0.50 | 0.50 |
| EDTA | 0.10 | 0.10 | 0.10 | 0.10 |
| Perfume | 0.25 | 0.25 | 0.25 | 0.25 |
| Water | 84.99 | 85.59 | 85.47 | 87.16 |

For Examples V through VII, water, stearamidopropyidimethyl-amine and the acid are mixed at temperature above 70° C. Then cetyl alcohol, stearyl alcohol and benzyl alcohol are added with agitation. After cooled down below 60° C., silicone mixture and perfume are added with agitation, then cooled down to about 30° C.

As the acid, for Example V and VII, L-glutamic acid is used, while for Examples VI and VII, lactic acid is used. For Example V, Glydant was added after silicone mixture, while for Examples VI through VII, Kathon CG is added. The obtained products show dry combing benefits and wet hair feel attributes.

Examples IX–XI

Hair rinse compositions of the present invention are prepared as follows:

| Component (Wt. %) | Ex. IX | Ex. X | Ex. XI |
|---|---|---|---|
| Stearamidoethyldiethylamine | 3.00 | 2.00 | 3.00 |
| L-Glutamic Acid | 0.92 | 0.61 | — |
| Lactic Acid (90%) | — | — | 0.63 |
| Cetyl Alcohol | 3.00 | 4.20 | 3.00 |
| Stearyl Alcohol | 2.00 | 2.80 | 2.00 |
| Silicone Mixture A[*1] | 5.00 | 4.20 | 5.00 |
| Kathon CG[*3] | 0.03 | 0.03 | 0.03 |
| Benzyl Alcohol | 0.50 | 0.40 | 0.50 |
| EDTA | 0.10 | 0.10 | 0.10 |
| Perfume | 0.25 | 0.25 | 0.25 |
| Water | 85.20 | 85.41 | 85.49 |

For Examples IX through XI, water, stearamidoethyldiethylamine and the acid are mixed at temperature above 70° C. Then cetyl alcohol, stearyl alcohol and benzyl alcohol are added with agitation. After cooled down below 60° C., silicone mixture, Kathon CG and perfume were added with agitation, then cooled down to about 30° C.

As the acid, for Example IX and X, L-glutamic acid is used, while for Examples XI, lactic acid is used. The obtained products showed dry combing benefits and wet hair feel attributes.

All publications, patent applications, and issued patents mentioned hereinabove are hereby incorporated in their entirety by reference.

What is claimed is:

1. A hair conditioning composition comprising by weight:
    (a) from about 0.5% to about 5.0% of an amidoamine or mixture of amidoamines having the following general formula:

$$R^1CONH(CH_2)_mN(R^2)_2$$

wherein $R^1$ is a residue of $C_{11}$ to $C_{24}$ fatty acids, $R^2$ is a $C_1$ to $C_4$ alkyl, and m is an integer from 1 to 4;
    (b) from about 0.05% to about 2.0% of glutamic acid;
    (c) from about 0.1% to about 15% of a fatty compound selected from the group consisting of fatty alcohols, fatty acids, fatty alcohol derivatives, fatty acid derivatives, and mixtures thereof; and
    (d) water;
wherein the composition has a pH of from about 4.5 to about 6, and is substantially free of quaternary ammonium compounds.

2. The composition of claim 1 wherein the amidoamine is selected from the group consisting of stearamidopropyldimethylamine, stearamidoethyldiethylamine, and mixtures thereof.

3. The composition of claim 1, wherein the glutamic acid is L-glutamic acid.

4. The composition of claim 1 wherein the fatty compound is selected from the group consisting of saturated $C_{16}$–$C_{18}$ straight chain fatty alcohols, $C_{14}$–$C_{18}$ branched chain fatty alcohols, and mixtures thereof.

5. The composition of claim 4 wherein the fatty compound is selected from the group consisting of stearyl alcohol, cetyl alcohol, and mixtures thereof.

6. A hair conditioning composition comprising by weight:
    (a) from about 0.5% to about 5.0% of an amidoamine or mixture of amidoamines having the following general formula:

$$R^1CONH(CH_2)_mN(R^2)_2$$

wherein $R^1$ is a residue of $C_{11}$ to $C_{24}$ fatty acids, $R^2$ is a $C_1$ to $C_4$ alkyl, and m is an integer from 1 to 4;
    (b) from about 0.05% to about 2.0% of glutamic acid;
    (c) from about 0.1% to about 15% of a fatty compound selected from the group consisting of fatty alcohols, fatty acids, fatty alcohol derivatives, fatty acid derivatives, and mixtures thereof; and
    (d) water;
wherein the mole ratio of the amidoamine to the acid is about 1:0.3 to about 1:1.0, and wherein the composition is substantially free of quaternary ammonium compounds.

7. The composition of claim 6 wherein the amidoamine is selected from the group consisting of stearamidopropyldimethylamine, stearamidoethyldiethylamine, and mixtures thereof.

8. The composition of claim 6, wherein the glutamic acid is L-glutamic acid.

9. The composition of claim 6 wherein the fatty compound is selected from the group consisting of saturated $C_{16}$–$C_{18}$ straight chain fatty alcohols, $C_{14}$–$C_{18}$ branched chain fatty alcohols, and mixtures thereof.

10. The composition of claim 9 wherein the fatty compound is selected from the group consisting of stearyl alcohol, cetyl alcohol, and mixtures thereof.

11. The composition of claim 1 wherein the fatty compound is present at a level of from about 1% to about 10%.

12. The composition of claim 6, wherein the fatty compound is present at a level of from about 1% to about 10%.

* * * * *